United States Patent
Umehara et al.

(10) Patent No.: US 10,730,815 B2
(45) Date of Patent: Aug. 4, 2020

(54) METHOD OF PRODUCING PURIFIED STILBENE COMPOUNDS

(71) Applicant: MORINAGA & CO., LTD., Tokyo (JP)

(72) Inventors: Masahiro Umehara, Kanagawa-ken (JP); Ikuko Kurita, Kanagawa-ken (JP); Koji Yanae, Kanagawa-ken (JP); Masahiko Sai, Kanagawa-ken (JP)

(73) Assignee: MORINAGA & CO., LTD., Tokyo (JP)

( * ) Notice: Subject to any disclaimer, the term of this patent is extended or adjusted under 35 U.S.C. 154(b) by 0 days.

(21) Appl. No.: 14/884,911

(22) Filed: Oct. 16, 2015

(65) Prior Publication Data
US 2016/0115110 A1    Apr. 28, 2016

(30) Foreign Application Priority Data

Oct. 17, 2014    (JP) .................. 2014-212754

(51) Int. Cl.
| | | |
|---|---|---|
| *C07C 39/21* | (2006.01) | |
| *A61K 31/05* | (2006.01) | |
| *A61K 47/40* | (2006.01) | |
| *C07C 37/84* | (2006.01) | |

(52) U.S. Cl.
CPC .............. *C07C 39/21* (2013.01); *A61K 31/05* (2013.01); *A61K 47/40* (2013.01); *C07C 37/84* (2013.01)

(58) Field of Classification Search
CPC .......... C07C 39/21; C07C 37/84; A61K 47/40
USPC ........................................ 568/717
See application file for complete search history.

(56) References Cited

U.S. PATENT DOCUMENTS 3,965,206 A  *  6/1976  Montgomery ............ C07C 2/76
585/319

8,617,620 B2  *  12/2013  Matsui .................. A61K 8/347
424/725
2006/0111318 A1    5/2006  Okamoto

FOREIGN PATENT DOCUMENTS

| CN | 101721713 B | | 1/2012 |
|---|---|---|---|
| JP | 63027440 A | * | 2/1988 |
| JP | 2000-344622 A | | 12/2000 |
| JP | 2009-102298 A | | 5/2009 |
| JP | 2011-162539 A | | 8/2011 |
| JP | 2012-46448 A | | 3/2012 |
| JP | 2013-21950 A | | 2/2013 |
| WO | WO-2009/012551 A1 | | 1/2009 |
| WO | WO 2010064764 A1 | * | 6/2010 ........... C12N 9/0071 |

OTHER PUBLICATIONS

Database WPI Week 201023, Thomson Scientific, London, GB; AN 2010-B14210 XP002754442 including abstract of KR 2010-0006359A, published Jan. 19, 2010 (2 pages).
Sasaki et al., "Constituent of *Callistemon rigidus* showing an inhibitory effect on activated matrix metalloproteinase-2," Journal of Tohoku Pharmaceutical University. 57:61-65 (2010) (5 pages).
Rao et al., "Stereoselective Photodimerization of (E)-Stilbenes in Crystalline gamma-Cyclodextrin Inclusion Complexes," J Org Chem. 64(22):8098-8104 (1999).
Suresh et al., "Novel photohydration of trans-stilbenes and trans-anethole inside cyclodextrin nanocavity in aqueous medium," J Photochem Photobio A: Chemistry 206(1):40-45 (2009).
Communication pursuant to Article 94(3) EPC for European Patent Application No. 15190390.3 dated Jan. 2, 2018 (6 pages).

* cited by examiner

*Primary Examiner* — Shaojia A Jiang
*Assistant Examiner* — Everett White
(74) *Attorney, Agent, or Firm* — Clark & Ebling LLP

(57) ABSTRACT

The present invention is directed to provide a precipitate obtained by adding γ-cyclodextrin to a liquid containing a stilbene compound. The precipitate according to the present invention is used as the precipitate obtained by adding γ-cyclodextrin to the liquid containing a stilbene compound.

9 Claims, 3 Drawing Sheets

Fig. 1    Precipitation by α-CD (Pic)
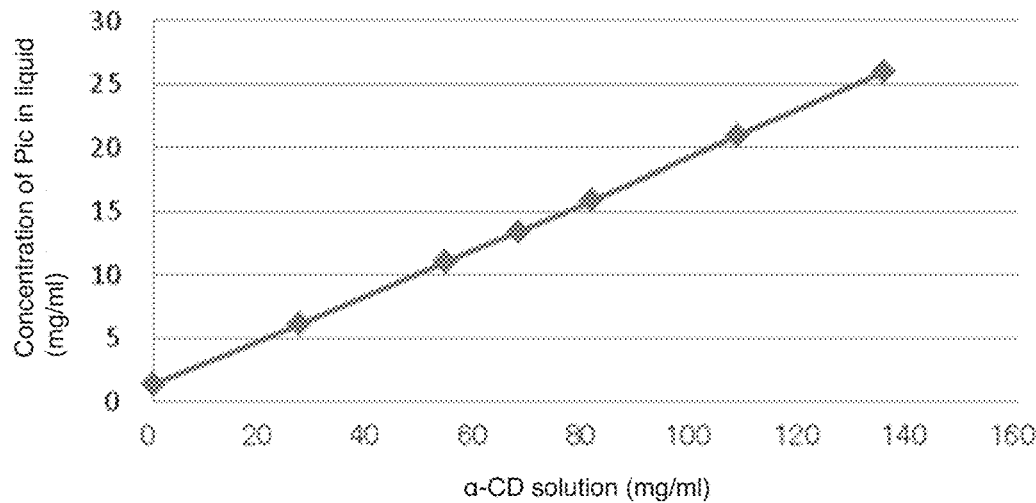
Fig. 2    Precipitation by β-CD (Pic)
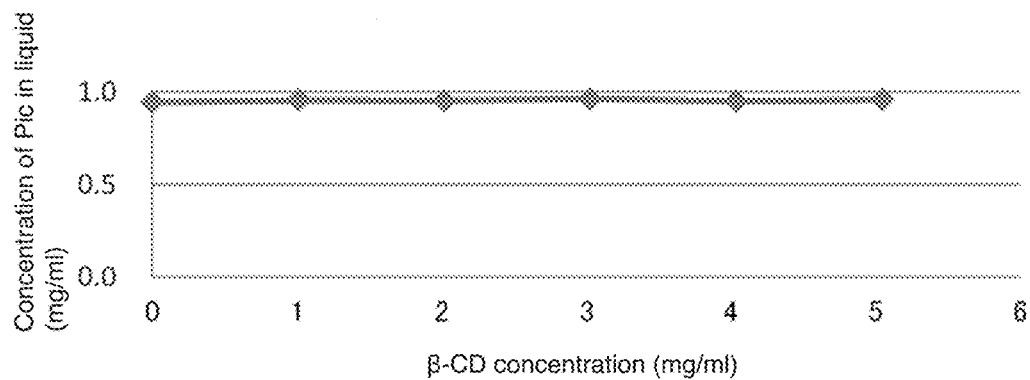
Fig. 3    Precipitation by γ-CD (Pic)
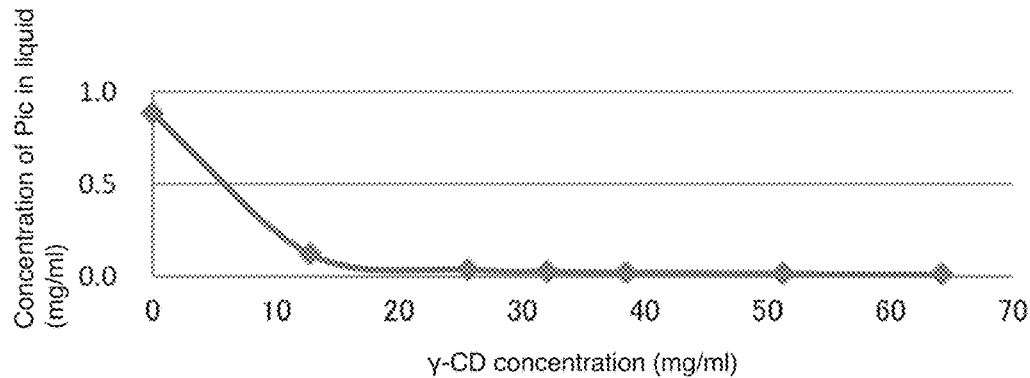

Fig. 4   Precipitation by γ-CD (Res)
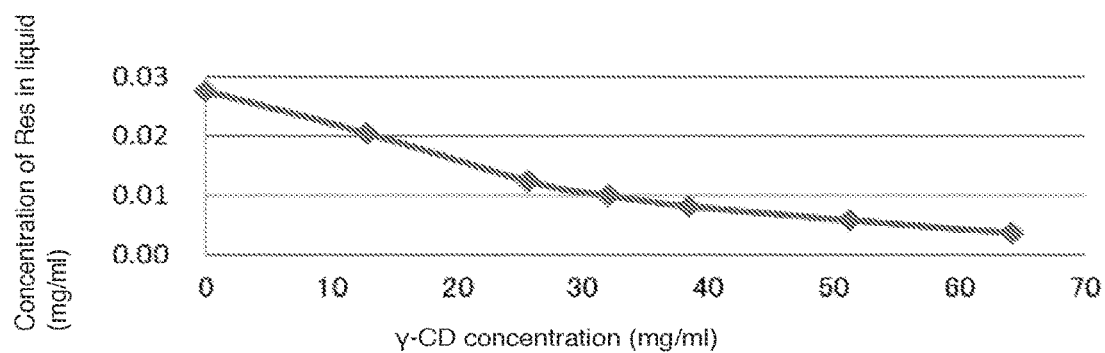
Fig. 5   Precipitation by γ-CD (Rha)
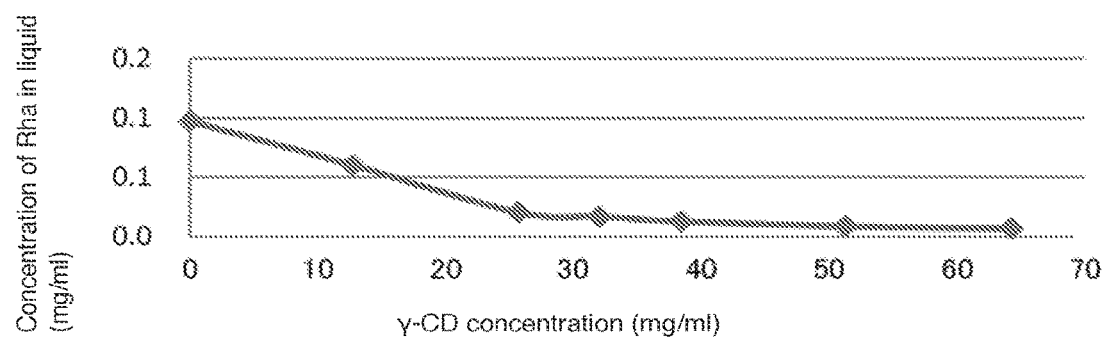
Fig. 6   Precipitation by γ-CD (Isorha)
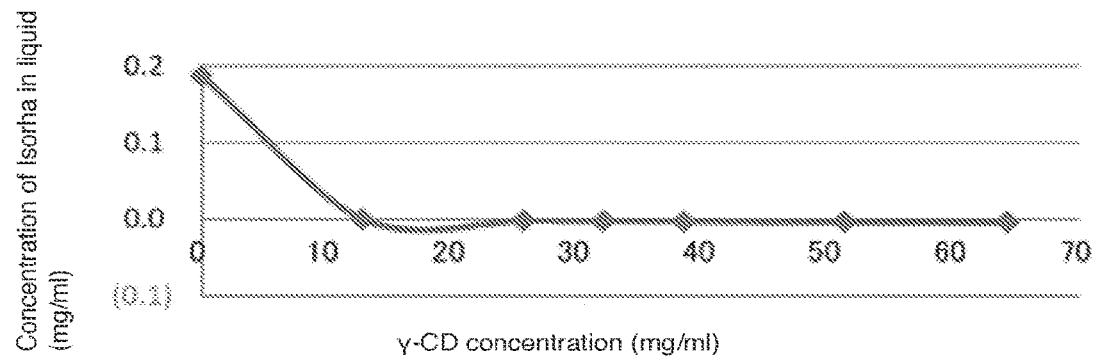

Fig. 7   Precipitation by γ-cyclodextrin vs. concentration of ethanol
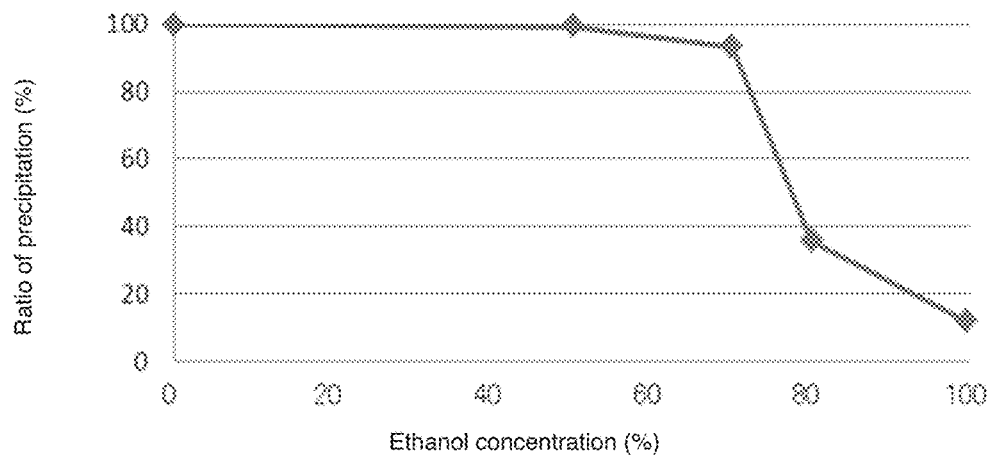
Fig. 8   Precipitation by γ-CD in extract materials containing ethanol at different concentrations
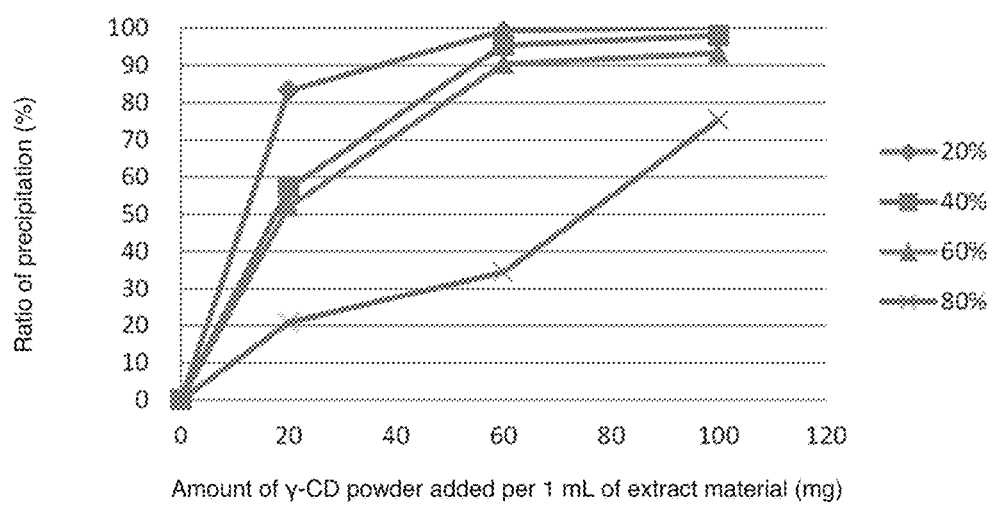

METHOD OF PRODUCING PURIFIED STILBENE COMPOUNDS

CROSS-REFERENCE TO A RELATED APPLICATION

This application claims the benefit of Japanese Patent Application No. 2014-212754 filed on Oct. 17, 2014, the entire disclosure of which is hereby incorporated by reference.

TECHNICAL FIELD

The present invention relates to methods of producing purified stilbene compounds.

BACKGROUND ART

Polyphenols have found applications in various fields, such as pharmaceuticals, cosmetics, and foods, because of their properties.

Piceatannol, for example, is a stilbene compound which is a type of polyphenols. It is contained in the seeds of the passion fruit, i.e., a fruit of the *Passiflora* genus in the Passifloraceae family, and has been reported to suppress the production of melanin, a major cause of brown spots, freckles, and pigmentation owing to sunburn (Japanese patent laid-open No. 2009-102298).

Piceatannol is also found in *Rhodomyrtus tomentosa* and *Callistemon rigidus* genera, which are small and large evergreen shrubs, respectively, in the Myrtaceae family. Extracts from these shrubs have a positive effect on recovery from UV damage and an inhibitory effect on MMP-2. It has been reported that piceatannol is the active ingredient in such extracts (Japanese patent laid-open No. 2012-46448; Kenroh Sasaki et al., Journal of Tohoku Pharmaceutical University, 57, 61-65 (2010)).

In use, polyphenols are often processed by inclusion complexation with cyclodextrin (CD) to improve solubility, absorption, and taste. For example, the water solubility and intestinal absorption of stilbenes was improved by encapsulation in α-cyclodextrin (α-CD), β-cyclodextrin (β-CD), or a mixture of α-CD, β-CD and γ-cyclodextrin (γ-CD) (Japanese patent laid-open No. 2000-344622). The bitter taste of polyphenols was suppressed by inclusion complexation with a highly branched cyclodextrin (Japanese patent laid-open No. 2011-162539).

To use polyphenols in various fields, they have been purified from plant extracts using experimental equipment for enzyme addition, adsorption, and filtration (Japanese patent laid-open No. 2013-021950).

Problem to be Solved by the Present Invention

An object of the present invention is to provide novel methods of producing purified stilbene compounds.

SUMMARY OF THE INVENTION

The present inventors have made extensive efforts to develop easier and more convenient methods of producing purified stilbene compounds and, as a result, found that the addition of γ-cyclodextrin (γ-CD) to a liquid containing a stilbene compound results in a precipitate containing γ-CD and the stilbene compound and that the stilbene compound can be purified by separating the obtained precipitate.

An aspect of the present invention is a precipitate obtained by adding γ-cyclodextrin to a liquid containing a stilbene compound. The precipitate may have been separated from the liquid.

Another aspect of the present invention is a method of purifying a stilbene compound from a liquid containing a stilbene compound, comprising the steps of adding γ-cyclodextrin to the liquid to produce a precipitate; and separating the precipitate from the liquid. The purified stilbene compound may be solid.

One aspect of the present invention is a method of producing a purified stilbene compound from a liquid containing a stilbene compound, comprising the steps of adding γ-cyclodextrin to the liquid to produce a precipitate; and separating the precipitate from the liquid. The liquid may be a plant extract material. The liquid may be an extract material obtained from passion fruit seeds, rose myrtle, or stiff bottlebrush. The liquid may contain an organic solvent. The method may further comprise the step of adding water, anhydrous organic solvent, or water-containing organic solvent to the separated precipitate. The organic solvent may be alcohol. The alcohol may be ethanol.

BRIEF DESCRIPTION OF THE DRAWINGS

FIG. 1 is a graph showing precipitation of piceatannol by α-cyclodextrin.

FIG. 2 is a graph showing precipitation of piceatannol by β-cyclodextrin.

FIG. 3 is a graph showing precipitation of piceatannol by γ-cyclodextrin.

FIG. 4 is a graph showing precipitation of resveratrol by γ-cyclodextrin.

FIG. 5 is a graph showing precipitation of rhapontigenin by γ-cyclodextrin.

FIG. 6 is a graph showing precipitation of isorhapontigenin by γ-cyclodextrin.

FIG. 7 is a view showing the relation between the concentration of ethanol and precipitation activity of γ-cyclodextrin.

FIG. 8 is a view showing the relation between precipitation activity of γ-cyclodextrin and the concentration of ethanol in plant extract materials.

EMBODIMENTS FOR CARRYING OUT THE INVENTION

The objects, features, advantages, and ideas of the present invention are apparent to those skilled in the art from the description of this specification. Those skilled in the art can easily reproduce the present invention from the description herein. The embodiments and specific examples described below represent preferable aspects of the present invention, which are given for the purpose of illustration or explanation. The present invention is not limited thereto. It is obvious to those skilled in the art that various changes and modifications may be made according to the description of the present specification within the spirit and scope of the present invention disclosed herein.

(1) Stilbene Compounds

Stilbene compounds purified according to a method of the present invention generally refer to polyphenols having a stilbene skeleton. Examples include stilbene, piceatannol, scirpusin A, scirpusin B, scirpusin C, rhapontigenin, isorhapontigenin, pterostilbene, resveratrol, oxyresveratrol, piceid, astringin, rhaponticin, and s-viniferin. The stilbene compounds may be chemically synthesized or derived from natural sources such as plants.

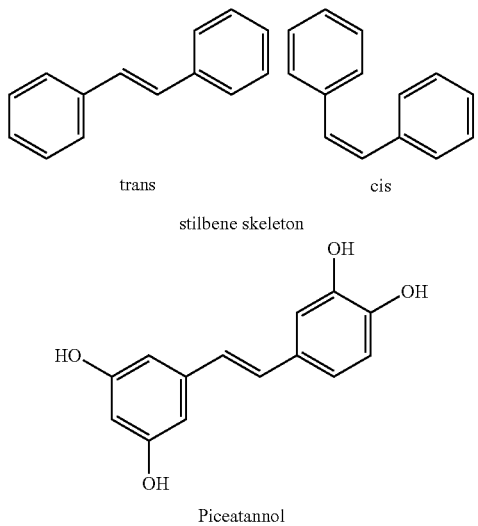

trans    cis stilbene skeleton

Piceatannol (2) Liquid Containing a Stilbene Compound

Purified stilbene compounds can be produced from liquids containing a stilbene compound according to a method of the present invention. Examples of liquids containing a stilbene compound include solutions obtained by dissolving a partially purified stilbene compound in a solvent or crude product such as a plant extract material. The solutions containing a stilbene compound may contain an organic solvent such as ethanol. For example, the concentration of the ethanol is not specifically limited; however it is preferably 80% or lower, more preferably 70% or lower, and most preferably 50% or lower. As used herein, the term "purified stilbene compound" refers to a stilbene compound with a higher purity produced from a liquid containing a stilbene compound with a lower purity. The purified stilbene compound is preferably solid. The purity of the stilbene compound refers to the weight percentage of the stilbene compound contained in the solid when the stilbene compound is provided as a solid, or the weight percentage of the stilbene compound contained in the solid obtained after removing a solvent when the stilbene compound is provided as a liquid. It is noted that the weight of a substance, such as cyclodextrin, added to the solid or the liquid containing a stilbene compound in a purification process is subtracted from the solid weight to calculate the purity. Purification is a procedure to increase purity.

Plant extract materials may be produced using a known method. For example, a plant may be dried, followed by crushing, grinding, or cutting to produce small pieces of, for example, seeds, which are then treated using a solvent. Then, residues are removed to produce an extract. This extract may be used without any further processing. Alternatively, an extract of a different purity or concentration may be used, which has been obtained by purifying a stilbene compound from an extract through one or more of the various methods or by diluting an extract using one or more of the various solvents. A solvent-free extract can be obtained by removing the solvent from the extract. The form of the solvent-free extract is not specifically limited. It may be, for example, a solid such as a powder, amorphous, or oil. As described above, any products afforded during the process of obtaining a solvent-free extract from a plant can be used as a plant extract material of the present invention. Alternatively, a solution obtained by dissolving the solvent-free extract in a solvent may be used as the plant extract material.

The type of the solvent used for the extraction can appropriately be selected by those skilled in the art. The solvent may be, for example, water; an organic solvent or an water-containing organic solvent, such as methanol, ethanol, acetone, ethyl acetate, glycerin, propylene glycol, dipropylene glycol, 1,3-butylene glycol, dimethyl sulfoxide, acetonitrile, N,N-dimethylformamide, 2-propanol, 1,4-dioxane, hexanes, chloroform, and dichloromethane; or a mixture of two or more solvents selected from the above. It is preferable that the solvent is water, ethanol, 1,3-butylene glycol or a mixture of two or more solvents selected therefrom. It is more preferable that the solvent is water, ethanol, or a hydrous ethanol which is a solvent mixture of water and ethanol. The term "water-containing organic solvent" as used herein indicates "organic solvent which contains water". The water added to the organic solvent to produce the water-containing organic solvent is not specifically limited and may be pure water or water with impurities, an acidic aqueous solution or alkaline aqueous solution, or a buffer solution containing various ions. In addition, the temperature of the solvent used for extraction can appropriately be selected from a range of temperatures within which the solvent retains its liquid properties.

The ratio of the solvents is not specifically limited when a solvent mixture is used. For example, when a solvent mixture of water and ethanol is used, the volume ratio of water and ethanol may be 1:99 to 99:1, preferably 3:97 to 80:20, more preferably 5:95 to 50:50, and particularly preferably 10:90 to 40:60.

When water or a solvent mixed with water is used as the solvent, it is preferable that the solvent is hot water or a solvent mixed with hot water. The water or the solvent mixed with water may contain a salt. The solvent containing a salt be a buffer, for example. The pH of the buffer is not specifically limited and may be acidic, neutral or alkaline. The buffer is preferably acidic, more preferably, acidic with a pH of 6 or lower, and still more preferably, acidic with a pH of from 1 to 5. The type of the salt in the buffer is not specifically limited. Examples include citrate, malate, phosphate, acetate, and carbonate.

The method of removing the solvent from an extract is not specifically limited and any known method can be used. For example, distillation under reduced pressure, freeze drying, or spray drying may be used. Freeze drying or spray draying is preferable and, spray drying is more preferable.

The plant used is not specifically limited as long as it contains a stilbene compound. Examples include fruits of passion flowers (e.g., *Passiflora edulis, Passiflora alata, Passiflora amethystina, Passiflora antioquiensis, Passiflora biflora, Passiflora buonapartea, Passiflora capsularis, Passiflora cearensis, Passiflora coccinea, Passiflora cochinchinensis, Passiflora filamentosa, Passiflora herbertiana, Passiflora laurifolia, Passiflora ligularis, Passiflora lunata, Passiflora lutea, Passiflora maliformis, Passiflora mixta, Passiflora mucronata, Passiflora mollissima, Passiflora nitida, Passiflora organensis, Passiflora pallida, Passiflora parahybensis, Passiflora pedata, Passiflora pinnatistipula, Passiflora popenovii, Passiflora quadrangularis, Passiflora riparia, Passiflora rubra, Passiflora serrato, Passiflora tiliaefolia, Passiflora tripartita, Passiflora villosa,* and *Passiflora warmingii*), rose myrtle (e.g., *Rhodomyrtus tomentosa*), bottlebrush (e.g., stiff bottlebrush *Callistemon speciosus*, and *Callistemon rigidus*), *Caragana tibetica*

(e.g., stem), Japanese knotweed (*Fallopia japonica*) (e.g., root), peanut (*Arachis hypogaea*), grape (*Vitaceae*) (e.g., fruit), blueberry (*Cyanococcus*) (e.g., fruit), deerberry (*Vaccinium stamineum*) (e.g., fruit), rice, wheat, barley, coffee, apple, artichoke, peanut, orange, pineapple, sweet potato, and burdock. It is preferable to use fruit of a passion flower, rose myrtle or bottlebrush which is known to have high content of piceatannol. The stilbene compound may be extracted from any part of the whole plant including, for example, fruit, flowers, seeds, leaves, branches, barks, trunks, stems, or roots may be used. It is preferable that the parts to be used are seeds for fruit of a passion flower, fruit for rose myrtle, and stems for bottlebrush.

(3) γ-Cyclodextrin

Three forms of cyclodextrin (CD), α, β, and γ as indicated below, are known. The cyclodextrin used in the method according to the present invention is γ-cyclodextrin (γ-CD).

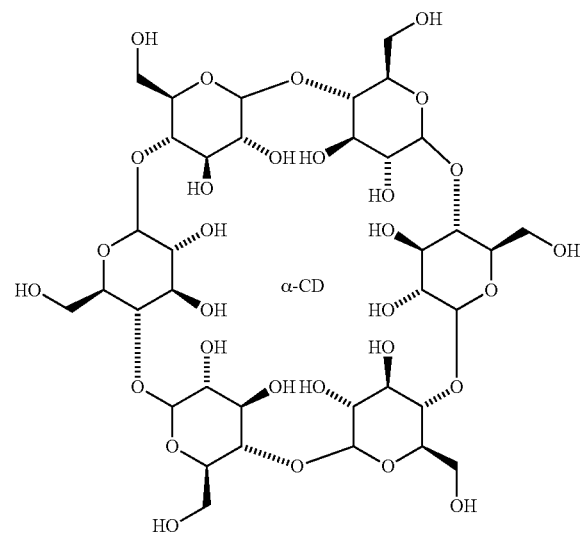

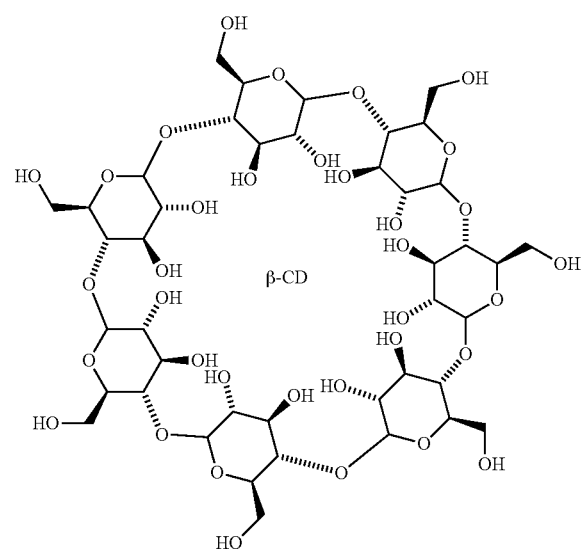

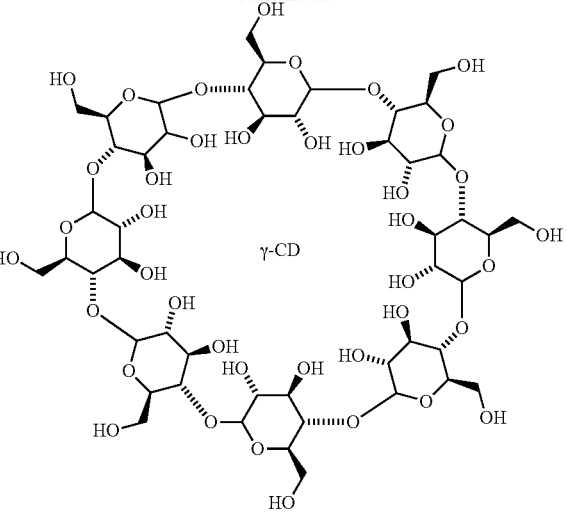

While γ-CD may be chemically synthesized by a known method, commercial compounds are easily available.

(4) Production of Purified Stilbene Compounds

According to the production method according to the present invention, when γ-CD is added to a liquid containing a stilbene compound represented by piceatannol and the mixture is stirred, a precipitate is produced which contains γ-CD and the stilbene compound. Subsequently, the solution containing the precipitate is stirred as required and then subjected to centrifugation or allowed to stand, followed by filtration, decantation, or suction to remove the supernatant and separate the precipitate. The addition of an organic solvent, such as alcohol represented by ethanol to the precipitate causes the stilbene compound in the precipitate to be released from the precipitate into the organic solvent. This organic solvent containing the precipitate is then stirred as required and then subjected to centrifugation or allowed to stand to precipitate γ-CD in the organic solvent, followed by filtration, decantation, or suction to collect the organic solvent containing the free stilbene compound released from the precipitate, thereby removing γ-CD from the organic solvent. In this way, a purified stilbene compound solution containing a high purity of stilbene compound can be obtained. In addition, by removing the organic solvent from this solution, a purified stilbene compound in solid form can easily be produced. The steps to dissolve the resultant solid stilbene compound, for example, in a buffer and further purify the stilbene compound using γ-CD may be repeated, thereby increasing the purity of the stilbene compound. For the separation of the stilbene compound from γ-CD, the stilbene compound may be purified by mixing the precipitate containing γ-CD and the stilbene compound with a solvent, such as water, dissolving the precipitate in the solvent, and then separating the stilbene compound by column chromatography using known equipments.

As used herein, the term "precipitate" refers to a solid that is present in a liquid but not dissolved. The precipitate includes a solid that has settled out on the bottom of a container in which the liquid is held, as well as a solid dispersed in the liquid. The solid is not specifically limited in its size, shape, structure, or composition as long as it is not dissolved in the liquid. For example, the precipitate can be separated from the liquid using centrifugation at 15,000 rpm for 10 minutes or more.

It is noted that γ-CD added to the liquid containing a stilbene compound may be in powder form or a solution containing γ-CD. The temperature of the liquid containing a stilbene compound upon the addition of γ-CD or stirring is not specifically limited. The time for stirring is not specifically limited either.

The purified stilbene compound thus produced can be used for pharmaceuticals (including medicines and reagents), quasi drugs, cosmetics, or foods.

EXAMPLES

Example 1

Precipitation of a Stilbene Compound by Different Cyclodextrins (CDs)

Precipitation of a stilbene compound by α-cyclodextrin (α-CD), β-cyclodextrin (β-CD) and γ-cyclodextrin (γ-CD) was examined. In this example, piceatannol was used as the stilbene compound.
(1) Precipitation of Piceatannol by α-CD α-CD solutions of six different concentrations as shown in Table 1 were prepared. Next, 300 μl of the prepared α-CD solution or pure water was added to 10 mg of piceatannol (denoted as "Pic" in the figure), which was stirred under light shielding conditions at 25° C. for 24 hours. Subsequently, the stirred solutions were subjected to centrifugation at 15,000 rpm at 25° C. for 5 minutes to collect the supernatants. The concentrations of piceatannol contained in the supernatants were measured using HPLC. The HPLC conditions are as follows.
[HPLC Conditions]
Column: Mightysil RP-18 GP250-10; diameter: 10 mm, length: 250 mm (Kanto Chemical Co., Inc.)
Column temperature: 40° C.
Elution conditions: flow rate: 3 mL/min, 0% methanol/100% pure water to 30% methanol/70% pure water (gradient, 10 min)
UV detection: 280 nm The results are given in Table 1 and FIG. 1.

TABLE 1

| α-CD (mg/mL) | Concentration of Pic in liquid (mg/mL) |
| --- | --- |
| 0 | 1.4 |
| 27.0 | 6.1 |
| 54.1 | 11.0 |
| 67.6 | 13.4 |
| 81.1 | 15.8 |
| 108.2 | 20.9 |
| 135.2 | 26.0 |

As seen from Table 1 and FIG. 1, the concentration of piceatannol was found to increase with the increase in concentration of the added α-CD solution.

As is clear from the above, piceatannol does not precipitate with α-CD.
(2) Precipitation of Piceatannol by β-CD β-CD solutions of five different concentrations (3.37, 6.73, 10.10, 13.46, 16.83 mg/mL) were prepared. Piceatannol was then added to pure water in the amount enough to precipitate, which was stirred under light shielding conditions at room temperature for 4 hours. The solutions were then subjected to centrifugation at 3,000 rpm at room temperature for 10 minutes. A saturated solution of piceatannol obtained by passing the resultant supernatant through a filter of 0.22 μm pore size was then mixed with pure water or each of the prepared β-CD solutions in a volume ratio of 7:3. The final β-CD concentrations of the mixed solutions are given in Table 2.

The mixed solutions were stirred under light shielding conditions at 25° C. for 24 hours. Subsequently, they were subjected to centrifugation at 15,000 rpm at 25° C. for 5 minutes to collect the supernatants. The concentrations of piceatannol contained in the supernatants were measured using HPLC as in the case of (1).

The results are given in Table 2 and FIG. 2.

TABLE 2

| β-CD (mg/mL) | Concentration of Pic in liquid (mg/mL) |
| --- | --- |
| 0 | 0.94 |
| 1.0 | 0.95 |
| 2.0 | 0.95 |
| 3.0 | 0.96 |
| 4.0 | 0.95 |
| 5.0 | 0.96 |

* β-CD is indicated at final concentrations

As seen from Table 2 and FIG. 2, the concentration of piceatannol did not change after the addition of β-CD.

As is clear from the above, piceatannol does not precipitate with β-CD.
(3) Precipitation of Piceatannol by γ-CD γ-CD solutions of six different concentrations (42.78, 85.56, 106.95, 128.33, 171.11, 213.89 mg/mL) were prepared. A saturated solution of piceatannol was then mixed with pure water or each of the prepared γ-CD solutions in a volume ratio of 7:3. The final γ-CD concentrations of the mixed solutions are given in Table 3.

The mixed solutions were stirred under light shielding conditions at 25° C. for 24 hours. Subsequently, they were subjected to centrifugation at 15,000 rpm at 25° C. for 5 minutes to collect the supernatants. These supernatants were further subjected to centrifugation using the same conditions to obtain another batch of supernatants. The concentrations of piceatannol contained in the supernatants from the second centrifugation were measured using HPLC as in the case of (1). The results are given in Table 3 and FIG. 3.

TABLE 3

| γ-CD (mg/mL) | Concentration of Pic in liquid (mg/mL) |
| --- | --- |
| 0 | 0.88 |
| 12.8 | 0.12 |
| 25.7 | 0.036 |
| 32.1 | 0.026 |
| 38.5 | 0.021 |
| 51.3 | 0.014 |
| 64.2 | 0.011 |

* γ-CD is indicated at final concentrations

As seen from Table 3 and FIG. 3, the addition of γ-CD resulted in a rapid decrease in the concentrations of piceatannol in the supernatants. As the amount of added γ-CD was increased, the concentration of piceatannol in the supernatant further decreased.

As is clear from the above, the addition of γ-CD leads to precipitation of piceatannol. Accordingly, piceatannol can be separated from the supernatant by centrifugation.

As shown in the above experiments, piceatannol does not precipitate either by the addition of α-CD or by the addition of β-CD whereas the addition of γ-CD to the liquid containing piceatannol results in a precipitate containing γ-CD and piceatannol.

Example 2

Precipitation of Various Stilbene Compounds by γ-CD (1) Method

Resveratrol (denoted by "Res" in the figure), rhapontigenin (denoted by "Rha" in the figure), and isorhapontigenin (denoted by "Isorha" in the figure) were used as the stilbene compounds to prepare respective solutions of the stilbene compounds. To each solution, γ-CD was added. Precipitation of these stilbene compounds by γ-CD and the relation between the concentration of γ-CD and the precipitation of the stilbene compounds were examined. Procedures for the preparation of the solutions and the measurement using HPLC were similar to those described in the above Example 1(3).

Chemical formulae of the stilbene compounds used are as follows.

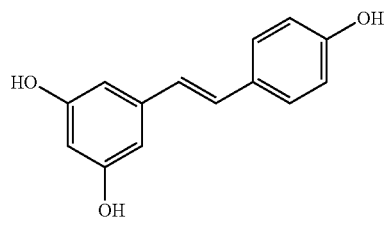

Resveratrol

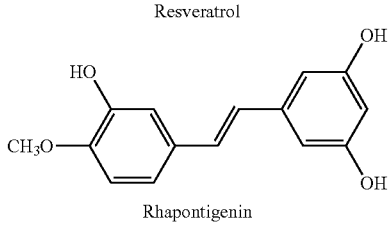

Rhapontigenin

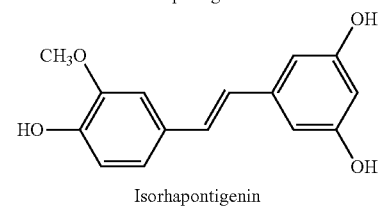

Isorhapontigenin (2) Results

Results for these stilbene compounds are shown in Tables 4 to 8 and FIGS. 4 to 8.

TABLE 4

| γ-CD (mg/mL) | Concentration of Res in liquid (mg/mL) |
| --- | --- |
| 0 | 0.028 |
| 12.8 | 0.020 |
| 25.7 | 0.012 |
| 32.1 | 0.010 |
| 38.5 | 0.0082 |

TABLE 4-continued

| γ-CD (mg/mL) | Concentration of Res in liquid (mg/mL) |
| --- | --- |
| 51.3 | 0.0058 |
| 64.2 | 0.0037 |

* γ-CD is indicated at the final concentrations

TABLE 5

| γ-CD (mg/mL) | Concentration of Rha in liquid (mg/mL) |
| --- | --- |
| 0 | 0.097 |
| 12.8 | 0.060 |
| 25.7 | 0.020 |
| 32.1 | 0.017 |
| 38.5 | 0.013 |
| 51.3 | ≤0.010 |
| 64.2 | ≤0.010 |

* γ-CD is indicated at the final concentrations

TABLE 6

| γ-CD (mg/mL) | Concentration of Isorha in liquid (mg/mL) |
| --- | --- |
| 0 | 0.19 |
| 12.8 | 0.0 |
| 25.7 | 0.0 |
| 32.1 | 0.0 |
| 38.5 | 0.0 |
| 51.3 | 0.0 |
| 64.2 | 0.0 |

* γ-CD is indicated at the final concentrations

As seen from Tables 4 to 6 and FIGS. 4 to 6, with the various stilbene compounds other than piceatannol, the addition of γ-CD to the liquids containing the stilbene compounds results in production of precipitates containing γ-CD and the stilbene compounds.

Example 3

Relation Between Precipitation by γ-CD and Concentration of Organic Solvent

The effect of the concentration of an organic solvent on the precipitation of a stilbene compound by γ-CD was examined. Ethanol (EtOH) was used as the organic solvent.

(1) Methods 100 mg of γ-CD was added to piceatannol solutions obtained by dissolving piceatannol in 500 μl of aqueous solutions of ethanol having five different concentrations shown in Table 9. The mixtures were stirred under light shielding conditions at 4° C. for 2 hours and then centrifuged under the same conditions as above to collect the supernatants. The concentrations of piceatannol in the collected supernatants were then measured using HPLC under the same conditions as above.

(2) Results

The results are given in Table 8 and FIG. 8. The ratios of precipitation were calculated using the following equation.

Ratio of precipitation=100−([concentration of piceatannol in supernatant]/[concentration of piceatannol before addition of γ-CD]×100)

TABLE 7

| EtOH concentration (%) | Ratio of precipitation (%) |
|---|---|
| 0 | ≥99.3 |
| 50 | 99.3 |
| 70 | 99.3 |
| 80 | 35.8 |
| 99.5 | 12.0 |

From Table 7 and FIG. 7, regardless of the concentration of ethanol, the addition of γ-CD resulted in production of a precipitate containing γ-CD and piceatannol. In particular, considerably high ratios of precipitation were observed for ethanol concentrations of at least 70% or lower.

Example 4

Effect of Addition of γ-CD on Precipitation of Piceatannol in Plant Extract Materials and Alcohol Concentration (1) Methods Gamma-CDs in the amounts given in Table 8 were mixed with an extract material of passion fruit seeds, obtained using water-containing ethanol. The extract material of the passion fruit seeds was obtained as follows. Passion fruit seeds were roasted and ground, and 80%, 60%, 40%, and 20% water-containing ethanols (compositions of water-containing ethanol are 80 v/v % ethanol+20 v/v % water, 60 v/v % ethanol+40 v/v % water, 40 v/v % ethanol+60 v/v % water, and 20 v/v % ethanol+80 v/v % water respectively) were added and mixed. The mixtures were stirred followed by filtration to separate the solid and liquid to thereby obtain extract materials of the passion fruit seeds. The ethanol solutions of the extract material were stirred under light shielding conditions at 4° C. for 2 hours and centrifuged at 15,000 rpm at 4° C. for 5 minutes to obtain the supernatants. Then, the concentrations of free piceatannol in the supernatants were measured using HPLC under the same condition as above.

(2) Results

Results are shown in Table 8 and FIG. 8. The ratios of precipitation were obtained using the same equation as above.

TABLE 8

| EtOH concentration (%) | γ-CD (mg) | Ratio of precipitation (%) |
|---|---|---|
| 20 | 0 | 0 |
|  | 20 | 83.2 |
|  | 60 | 99.3 |
|  | 100 | 100.4 |
| 40 | 0 | 0 |
|  | 20 | 57.1 |
|  | 60 | 95.4 |
|  | 100 | 98.0 |
| 60 | 0 | 0 |
|  | 20 | 52.1 |
|  | 60 | 90.4 |
|  | 100 | 93.3 |
| 80 | 0 | 0 |
|  | 20 | 20.8 |
|  | 60 | 34.5 |
|  | 100 | 75.2 |

As shown in Table 8 and FIG. 8, the precipitation of the stilbene compound by γ-CD is independent of the concentration of ethanol. In particular, a large effect of precipitation is obtained at ethanol concentrations of at least 60% or lower.

Example 5

Purification of Stilbene Compound from Plant Extract Material Using γ-CD (1) Methods First, 1.95 g of γ-CD was added to 30 mL of extract material of passion fruit seeds. Then, the mixture was stirred under light shielding conditions at room temperature for 13.5 hours and centrifuged at 3,000 rpm for 10 minutes, followed by the removal of the supernatant obtained. The precipitate obtained from the centrifugation was freeze-dried, and 10 mL of ethanol was added thereto. The mixture was stirred under light shielding conditions at room temperature for 10 minutes and centrifuged at 3,000 rpm for 10 minutes, and the supernatant obtained was recovered. The recovered supernatant was concentrated and dried using an evaporator to produce a solid, solvent-free extract. The concentrations of piceatannol in the extract material from the seeds of the passion fruit and in the solvent-free extract before the examinations were measured using HPLC under the same conditions as above, after diluting the extract material and the solvent-free extract to a predetermined dilution factor.

(2) Results

The purity of piceatannol in the extract material from the seeds of passion fruit before the experiments was 10.5%, whereas that in the solvent-free extract was 64.2%. This indicates that the method according to the present invention led to a 6.1-fold increase in the purity of piceatannol. Each purity value was obtained as a percentage of piceatannol weight per weight of solid in the extract material or in the solvent-free solid by calculating the weight of piceatannol in the extract material or in the solvent-free extract from the measured concentration of piceatannol.

INDUSTRIAL APPLICABILITY

The present invention can provide novel methods of producing purified stilbene compounds.

The invention claimed is:

1. A method of purifying piceatannol from a liquid containing piceatannol, comprising the steps of:
    adding γ-cyclodextrin to the liquid to produce a precipitate comprising γ-cyclodextrin and piceatannol;
    separating the precipitate from the liquid;
    adding an organic solvent to the precipitate to release piceatannol from the precipitate into the organic solvent; and collecting the organic solvent containing piceatannol released from the precipitate to separate piceatannol from the γ-cyclodextrin in the precipitate.

2. The method according to claim 1, wherein the purified piceatannol is solid.

3. A method of producing a purified piceatannol from a liquid containing piceatannol, comprising the steps of:
    adding γ-cyclodextrin to the liquid to produce a precipitate comprising γ-cyclodextrin and piceatannol;
    separating the precipitate from the liquid;
    adding an organic solvent to the precipitate to release the piceatannol from the precipitate into the organic solvent; and collecting the organic solvent containing piceatannol released from the precipitate to separate piceatannol from the γ-cyclodextrin in the precipitate.

4. The method according to claim 3, wherein the liquid is a plant extract material.

5. The method according to claim 4, wherein the liquid is an extract material obtained from passion fruit seeds, rose myrtle, or stiff bottlebrush.

6. The method according to claim 3, wherein the liquid contains an organic solvent.

7. The method according to claim 6, wherein the organic solvent is alcohol.

8. The method according to claim 7, wherein the alcohol is ethanol.

9. The method according to claim 3, further comprising the step of adding water, anhydrous organic solvent, or water-containing organic solvent to the separated precipitate.

* * * * *